US009293326B2

(12) United States Patent
Steiger et al.

(10) Patent No.: US 9,293,326 B2
(45) Date of Patent: Mar. 22, 2016

(54) METHOD FOR PRODUCING INDIUM OXIDE-CONTAINING LAYERS

(71) Applicants: Juergen Steiger, Taipei (TW); Dennis Fruehling, Marl (DE); Alexey Merkulov, Recklinghausen (DE); Arne Hoppe, Herne (DE)

(72) Inventors: Juergen Steiger, Taipei (TW); Dennis Fruehling, Marl (DE); Alexey Merkulov, Recklinghausen (DE); Arne Hoppe, Herne (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/407,681

(22) PCT Filed: Jun. 4, 2013

(86) PCT No.: PCT/EP2013/061452
§ 371 (c)(1),
(2) Date: Dec. 12, 2014

(87) PCT Pub. No.: WO2013/186082
PCT Pub. Date: Dec. 19, 2013

(65) Prior Publication Data
US 2015/0170913 A1 Jun. 18, 2015

(30) Foreign Application Priority Data

Jun. 13, 2012 (DE) .................. 10 2012 209 918

(51) Int. Cl.
*H01L 29/02* (2006.01)
*H01L 21/02* (2006.01)
(Continued)

(52) U.S. Cl.
CPC .......... *H01L 21/02565* (2013.01); *C07F 5/003* (2013.01); *C23C 18/1216* (2013.01);
(Continued)

(58) Field of Classification Search
CPC . H01L 21/288; H01L 21/02628; H01L 29/22; H01L 29/43
USPC ...................... 438/609; 257/43, 749
See application file for complete search history.

(56) References Cited

U.S. PATENT DOCUMENTS 8,546,594 B2 10/2013 Steiger et al.
8,841,164 B2 9/2014 Steiger et al.
(Continued)

FOREIGN PATENT DOCUMENTS

| WO | WO 2011/020781 A1 | 2/2011 |
| WO | WO 2012/010427 A1 | 1/2012 |
| WO | WO 2013/050221 A1 | 4/2013 |

OTHER PUBLICATIONS

International Search Report issued Jun. 6, 2014 in PCT/EP2013/061452.
N. Ya Turova, "Metal oxoalkoxides. Synthesis, properties and structures", Russian Chemical Reviews, vol. 73, No. 11, 2004 Russian Academy of Sciences and Turpion Ltd., XP009141757, (Jan. 2004), pp. 1041-1064.

*Primary Examiner* — Michael Lebentritt
(74) *Attorney, Agent, or Firm* — Oblon, McClelland, Maier & Neustadt, L.L.P.

(57) ABSTRACT

The present invention relates to a fluid phase method for producing indium oxide-containing layers, in which a composition comprising at least one indium oxo-alkoxide of the generic formula $M_xO_y(OR)_z[O(R'O)_eH]_aX_bY_c[R''OH]_d$ with $x=3-25$, $y=1-10$, $z=3-50$, $a=0-25$, $b=0-20$, $c=1-20$, $d=0-25$, $e=0, 1$, M=In, R, R', R''=organic remainder, X=F, Cl, Br, I, and Y=—$NO_3$, —$NO_2$, where b+c is =1-20 and at least one solvent is applied to a substrate, optionally dried, and converted into an indium oxide-containing layer, to the indium oxo-alkoxides of the indicated generic formula, to coating compositions comprising said indium oxo-alkoxides, to layers that can be produced by means of the method according to the invention, and to the use of said layers.

18 Claims, 2 Drawing Sheets

(51) Int. Cl.
*C23C 18/12* (2006.01)
*C23C 18/14* (2006.01)
*H01L 31/18* (2006.01)
*C07F 5/00* (2006.01)
*H01L 21/477* (2006.01)
*H01L 29/24* (2006.01)

(52) U.S. Cl.
CPC .............. *C23C18/1295* (2013.01); *C23C 18/14* (2013.01); *H01L 21/02628* (2013.01); *H01L 21/477* (2013.01); *H01L 29/24* (2013.01); *H01L 31/1884* (2013.01); *C23C 18/1254* (2013.01); *C23C 18/1279* (2013.01); *Y02E 10/50* (2013.01)

(56) References Cited

U.S. PATENT DOCUMENTS

| | | | |
|---|---|---|---|
| 8,859,332 | B2 | 10/2014 | Steiger et al. |
| 2011/0309313 | A1 | 12/2011 | Steiger et al. |
| 2011/0315982 | A1 | 12/2011 | Hoppe et al. |
| 2012/0181488 | A1* | 7/2012 | Steiger et al. .............. 252/519.1 |
| 2012/0202318 | A1 | 8/2012 | Steiger et al. |
| 2013/0104773 | A1* | 5/2013 | Steiger et al. ............ 106/287.18 |
| 2013/0116463 | A1 | 5/2013 | Steiger et al. |
| 2013/0221352 | A1* | 8/2013 | Steiger et al. ................... 257/43 |
| 2015/0053966 | A1 | 2/2015 | Steiger et al. |

\* cited by examiner

METHOD FOR PRODUCING INDIUM OXIDE-CONTAINING LAYERS

The invention relates to a process for producing indium oxide-containing layers, to precursors and coating compositions usable in the process, to the layers producible by the process and to the use thereof.

Indium oxide (indium(III) oxide, $In_2O_3$), owing to the large band gap between 3.6 and 3.75 eV (measured for vapour-deposited layers) [H. S. Kim, P. D. Byrne, A. Facchetti, T. J. Marks; *J. Am. Chem. Soc.* 2008, 130, 12580-12581], is a promising semiconductor. Thin films of a few hundred manometers in thickness may additionally have a high transparency in the visible spectral range of greater than 90% at 550 nm. In extremely highly ordered single indium oxide crystals, it is additionally possible to measure charge carrier mobilities of up to 160 $cm^2/Vs$.

Indium oxide is often used in particular together with tin (IV) oxide ($SnO_2$) as the semiconductive mixed oxide ITO. Owing to the comparatively high conductivity of ITO layers with the same transparency in the visible spectral range, one application thereof is in the field of liquid-crystal displays (LCDs), especially as a "transparent electrode". These usually doped metal oxide layers are produced industrially in particular by costly vapour deposition methods under high vacuum.

Indium oxide-containing layers and the production thereof, especially ITO layers and pure indium oxide layers, and the production thereof, are thus of great significance for the semiconductor and display industry.

Possible reactants and precursors discussed for the synthesis of indium oxide-containing layers include a multitude of compound classes. Examples include indium salts. For instance, Marks et al. describe components produced using a precursor solution composed of $InCl_3$ and the base monoethanolamine (MEA) dissolved in methoxyethanol. After spin-coating of the solution, the corresponding indium oxide layer is obtained by thermal treatment at 400° C. [H. S. Kim, P. D. Byrne, A. Facchetti, T. J. Marks; *J. Am. Chem. Soc.* 2008, 130, 12580-12581 and supplemental information].

Elsewhere, possible reactants or precursors discussed for the indium oxide synthesis are indium alkoxides. An indium alkoxide is a compound consisting of at least one indium atom, at least one alkoxide radical of the formula —OR (R=organic radical) and optionally one or more organic radicals —R, one or more halogen radicals and/or one or more —OH or —OROH radicals.

Independently of a possible use for indium oxide formation, the prior art describes various indium alkoxides and indium oxo alkoxides. Compared to the indium alkoxides already mentioned, indium oxo alkoxides also have at least one further oxygen radical (oxo radical) bound directly to an indium atom or bridging at least two indium atoms.

Mehrotra et al. describe the preparation of indium tris-alkoxide $In(OR)_3$ from indium(III) chloride ($InCl_3$) with Na—OR where R is methyl, ethyl, isopropyl, n-, s-, t-butyl and pentyl radicals. [S. Chatterjee, S. R. Bindal, R. C. Mehrotra; *J. Indian Chem. Soc.* 1976, 53, 867].

A review article by Carmalt et al. (Coordination Chemistry Reviews 250 (2006), 682-709) describes various gallium(III) and indium(III) alkoxides and aryloxides, some of which may also be present with bridging by means of alkoxide groups. Additionally presented is an oxo-centred cluster of the formula $In_5(\mu$-$O)(O^iPr)_{13}$, more specifically $[In_5(\mu_5$-$O)(\mu_3$-$O^iPr)_4(\mu_2$-$O^iPr)_4(O^iPr)_5]$, which is an oxo alkoxide and cannot be prepared from $[In(O^iPr)_3]$.

A review article by N. Turova et al., Russian Chemical Reviews 73 (11), 1041-1064 (2004) summarizes synthesis, properties and structures of metal oxo alkoxides, which are considered therein as precursors for the production of oxidic materials via sol-gel technology. In addition to a multitude of other compounds, the synthesis and structure of $[Sn_3O(O^tBu)_{10}(^tBuOH)_2]$, of the already mentioned compound $[In_5O(O^iPr)_{13}]$ and of $[Sn_6O_4(OR)_4]$ (R=Me, $Pr^i$) are described.

The article by N. Turova et al., Journal of Sol-Gel Science and Technology, 2, 17-23 (1994) presents results of studies on alkoxides, which are considered therein as a scientific basis for the development of sol-gel processes of alkoxides and alkoxide-based powders. In this context, there is also discussion of a purported "indium isopropoxide", which was found to be the oxo alkoxide with a central oxygen atom and five surrounding metal atoms of the formula $M_5(\mu$-$O)(O^iPr)_{13}$ which is also described in Carmalt et al.

A synthesis of this compound and the crystal structure thereof are described by Bradley et al., J. Chem. Soc., Chem. Commun., 1988, 1258-1259. Further studies by the authors led to the result that the formation of this compound cannot be attributed to a hydrolysis of intermediately formed $In(O^iPr)_3$ (Bradley et al., Polyhedron Vol. 9, No. 5, pp. 719-726, 1990). Suh et al., J. Am. Chem. Soc. 2000, 122, 9396-9404 additionally found that this compound is not preparable by a thermal route either from $In(O^iPr)_3$. Moreover, Bradley (Bradley et al., Polyhedron Vol. 9, No. 5, pp. 719-726, 1990) found that this compound cannot be sublimed.

Metal oxide layers can in principle be produced via various processes.

One means of producing metal oxide layers is based on sputtering techniques. However, these techniques have the disadvantage that they have to be performed under high vacuum. A further disadvantage is that the films produced therewith have many oxygen defects, which make it impossible to establish a controlled and reproducible stoichiometry of the layers and hence lead to poor properties of the layers produced.

Another means in principle for producing metal oxide layers is based on chemical gas phase deposition. For example, it is possible to produce indium oxide-containing layers from indium oxide precursors such as indium alkoxides or indium oxo alkoxides via gas phase deposition. For example U.S. Pat. No. 6,958,300 B2 teaches using at least one metal organo oxide precursor (alkoxide or oxo alkoxide) of the generic formula $M^1_q(O)_x(OR^1)_y$ (q=1-2; x=0-4, y=1-8, $M^1$=metal; e.g. Ga, In or Zn, $R^1$=organic radical; alkoxide when x=0, oxo alkoxide when ≥1) in the production of semiconductors or metal oxide layers by gas phase deposition, for example CVD or ALD. However, all gas phase deposition processes have the disadvantage that they require either i) in the case of a thermal reaction regime, the use of very high temperatures, or ii) in the case of introduction of the required energy for the decomposition of the precursor in the form of electromagnetic radiation, high energy densities. In both cases, it is possible only with a very high level of apparatus complexity to introduce the energy required to decompose the precursor in a controlled and homogeneous manner.

Advantageously, metal oxide layers are thus produced by means of liquid phase processes, i.e. by means of processes comprising at least one process step before the conversion to the metal oxide, in which the substrate to be coated is coated with a liquid solution of at least one precursor of the metal oxide, and optionally subsequently dried and converted. A metal oxide precursor is understood to mean a compound decomposable thermally or with electromagnetic radiation, with which metal oxide-containing layers can be formed in the presence or absence of oxygen or other oxidizing substances. Prominent examples of metal oxide precursors are, for example, metal alkoxides and metal oxo alkoxides. In principle, the layer can be produced i) by sol-gel processes in which the metal alkoxides used are converted first to gels in the presence of water by hydrolysis and subsequent condensation, and then to metal oxides, or ii) from nonaqueous solution via conversion.

The production of indium oxide-containing layers from indium alkoxides from the liquid phase also forms part of the prior art.

The production of indium oxide-containing layers from indium alkoxides via sol-gel processes in the presence of significant amounts of water forms part of the prior art. WO 2008/083310 A1 describes processes for producing inorganic layers or organic/inorganic hybrid layers on a substrate, in which a metal alkoxide (for example one of the generic formula $R^1M$-$(OR^2)_{y-x}$) or a prepolymer thereof is applied to a substrate, and then the resulting metal alkoxide layer is hardened in the presence of, and reacting with, water. The metal alkoxides usable may include those of indium, gallium, tin or zinc. However, indium oxide-containing layers producible by this process are very inhomogeneous, do not have satisfactory electrical properties and additionally, more particularly, have inadequate stability with respect to atmospheric influences and electrical stress.

JP 2007-042689 A describes metal alkoxide solutions which may contain indium alkoxides, and also processes for producing semiconductor components which use these metal alkoxide solutions. The metal alkoxide films are treated thermally and converted to the oxide layer. However, these systems too do not give sufficiently homogeneous films with sufficiently good electrical properties and sufficient stability with respect to atmospheric influences and electrical stress. Pure indium oxide layers additionally cannot be produced by the process described therein.

WO 2010/094581 A1 describes the use of indium alkoxides in the production of indium oxide-containing layers from anhydrous solutions. Although the resulting layers are more homogeneous than layers produced by means of sol-gel processes, the use of indium alkoxides in anhydrous systems still has the disadvantage that the conversion of indium alkoxide-containing formulations to indium oxide-containing layers does not give sufficiently good electrical performance or sufficient stability in relation to atmospheric influences and electrical stress in the resulting layer.

WO 2011/072887 A1 discloses a process for preparing indium halogen dialkoxides of the generic formula $InX(OR)_2$, and WO 2011/073005 A2 a liquid phase process for production of indium oxide-containing layers using compositions comprising at least one such indium halogen dialkoxide $InX(OR)_2$. However, the resulting indium alkoxide-containing layers—even if the electrical properties are already improved over the prior art cited so far—still do not have sufficiently good electrical properties or sufficient stability in relation to atmospheric influences and electrical stress. This may possibly be because chloride residues are imputed to lead to satisfaction of the valences of the oxygen in the resulting metal oxide semiconductor and hence to a reduction in electron mobility (Jeong et al., J. Phys. Chem. C 2011, 115, 11773-11780).

According to WO 2010/122274 A1, the stability of a metal oxide semiconductor can be increased by the addition of alkali metals or alkaline earth metals, but the resulting layers do not have good semiconductive properties.

Finally, WO 2011/020781 A1 describes a liquid phase process for production of indium oxide-containing layers using compositions comprising indium oxo alkoxides of the generic formula $M_xO_y(OR)_z[O(R'O)_cH]_aX_b[R"OH]_d$, which leads to indium oxide layers having controlled, homogeneous and reproducible stoichiometry, high homogeneity and better electrical performance. A disadvantage, however, is that these indium oxide-containing layers too still do not lead to sufficiently good electrical properties and in particular do not lead to sufficient stability in relation to atmospheric influences (more particularly with respect to oxygen and/or water present in the atmosphere) and electrical stress (more particularly still insufficient stability in negative bias stress).

It is thus an object of the present invention to provide a process for producing indium oxide-containing layers, which avoids the disadvantages of the prior art. More particularly, a process is to be provided which leads to indium oxide layers having controlled, homogeneous and reproducible stoichiometry, high homogeneity, good electrical performance and good stability with respect to atmospheric influences and electrical stress.

These objects are achieved by a liquid phase process for producing indium oxide-containing layers, in which a composition comprising i) at least one indium oxo alkoxide of the generic formula $M_xO_y(OR)_z[O(R'O)_eH]_aX_bY_c[R"OH]_d$ where M=In, x=3-25, y=1-10, z=3-50, a=0-25, b=0-20, c=1-20, d=0-25, e=0, 1, R, R', R"=organic radical, X=F, Cl, Br, I, Y=—$NO_3$, —$NO_2$, with the proviso that b+c=1-20, and ii) at least one solvent is applied to a substrate, optionally dried and converted to an indium oxide-containing layer. Preferred R, R' and R" radicals are C1-C15-alkyl, -alkoxyalkyl, -aryl or oxyarylalkyl groups (where the prefix C1-C15 in each case represents radicals having 1 to 15 carbon atoms), and particularly preferred R, R' and R" radicals are=—$CH_3$, —$CH_2CH_3$, —$CH_2CH_2OCH_3$, —$CH(CH_3)_2$, —$CH(CH_3)CH_2OCH_3$, —$C(CH_3)_3$ and

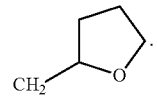

The liquid phase process according to the invention for producing indium oxide-containing layers from solution is a process comprising at least one process step in which the substrate to be coated is coated with a liquid solution containing at least one metal oxide precursor and is optionally then dried. More particularly, this is not a sputtering or CVD process. The liquid phase process according to the invention can be performed either with nonaqueous compositions or as a sol-gel process with aqueous compositions. The process according to the invention is preferably an anhydrous process. A metal oxide precursor is understood to mean a compound decomposable thermally or with electromagnetic radiation, with which metal oxide-containing layers can be formed in the presence or absence of oxygen or other oxidizing substances. Liquid compositions in the context of the present invention are understood to mean those which are in liquid form under SATP conditions ("Standard Ambient Temperature and Pressure"; T=25° C. and p=1013 hPa) and on application to the substrate to be coated. A nonaqueous solution or an anhydrous composition is understood here and hereinafter to mean a solution or formulation which has not more than 200 ppm of $H_2O$. Correspondingly, aqueous compositions have higher water contents.

The process product of the process according to the invention, the indium oxide-containing layer, is understood to mean a metal- or semimetal-containing layer which comprises indium atoms or ions present essentially in oxidic form. Optionally, the indium oxide-containing layer may also comprise carbene, halogen or alkoxide components from an incomplete conversion or an incomplete removal of by-products formed. This indium oxide-containing layer may be a pure indium oxide layer, i.e. neglecting any carbene, alkoxide or halogen components may consist essentially of indium atoms or ions present in oxidic form, or comprise proportions of further metals which may themselves be present in elemental or oxidic form. To obtain pure indium oxide layers, only indium-containing precursors should be used in the process according to the invention, preferably only indium oxo alkoxide compounds and optionally indium alkoxides. In contrast, to obtain layers comprising other metals in addition to the indium-containing precursors, it is also possible to use precursors of metals in the 0 oxidation state (to prepare layers containing further metals in uncharged form) or metal oxide precursors (for example other metal alkoxides or oxo alkoxides).

The inventive precursors of the generic formula $M_xO_y(OR)_z[O(R'O)_eH]_aX_bY_c[R"OH]_d$ which have not been described to date in the literature can be produced, for example, by reaction of $AgNO_3$ or of a compound which has a tendency to be ionic and the cation of which forms a sparingly soluble chloride compound in the reaction medium with compounds $M_xO_y(OR)_z[O(R'O)_eH]_aX_bY_c[R"OH]_d$, already known in the prior art, where x=3-25, y=1-10, z=3-50, a=0-25, b=0-20, c=0, 1, d=0-25, M=In, R, R', R"=organic radical, and X=F, Cl, Br, I. Also suitable is the reaction of $In_6O_2X_6(OR)_6(R'CH(O)COOR")_2(HOR)_x(HNR'''_2)_y$ (cf. WO 2012/010427 A1) or $In_7O_2(OH)(OR)_{12}X_4(ROH)_x$ (cf. WO 2012/010464 A1) with the same reagents. Also suitable is the synthesis from halogen-containing indium halogen dialkoxides of the generic formula $InX(OR)_2$ preparable according to WO 2011/072887 A1.

Particularly stable layers can be achieved with indium oxo alkoxides which essentially no longer have any halogen residues, i.e. with those compounds of the generic formula $M_xO_y(OR)_z[O(R'O)_eH]_aX_bY_c[R"OH]_d$, in which b=0.

Preferably, the indium oxo alkoxide is one of the generic formula $M_xO_y(OR)_zY_c$ where x=3-20, y=1-8, z=3-25, c=1-20, OR=C1-C15-alkoxy, -oxyalkylalkoxy, -aryloxy or oxyarylalkoxy group, Y=—$NO_3$, and more preferably one of the generic formula $M_xO_y(OR)_zY_c$ where x=3-15, y=1-5, z=10-20, c=4-10, R=—$CH_3$, —$CH_2CH_3$, —$CH_2CH_2OCH_3$, —$CH(CH_3)_2$, —$CH(CH_3)CH_2OCH_3$, —$C(CH_3)_3$ and/or

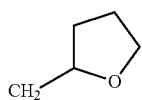

and Y=—$NO_3$. These have the advantage of being suitable for the production of layers having particularly good stability in relation to atmospheric influences and electrical stress.

Very particular preference is given to a process in which the indium oxo alkoxide used is preparable from a reactant of the generic formula $In(OCH_3)_2Cl$.

The present process according to the invention is particularly suitable for production of indium oxide layers when the indium oxo alkoxide is used as the sole metal oxide precursor. Very particularly suitable layers result when the sole metal oxide precursor has the generic formula $In_6O(OCH_2CH_2OCH_3)_{10}(NO_3)_6$.

The at least one indium oxo alkoxide is preferably present in proportions of 0.1 to 15% by weight, more preferably 1 to 10% by weight, most preferably 2 to 5% by weight, based on the total mass of the composition.

The composition further contains at least one solvent, i.e. the composition may contain either a solvent or a mixture of different solvents. Useable with preference in the formulation for the process according to the invention are aprotic and weakly protic solvents, i.e. those selected from the group of the aprotic nonpolar solvents, i.e. of the alkanes, substituted alkanes, alkenes, alkynes, aromatics without or with aliphatic or aromatic substituents, halogenated hydrocarbons, tetramethylsilane, the group of the aprotic polar solvents, i.e. of the ethers, aromatic ethers, substituted ethers, esters or acid anhydrides, ketones, tertiary amines, nitromethane, DMF (dimethylformamide), DMSO (dimethyl sulphoxide) or propylene carbonate, and the weakly protic solvents, i.e. the alcohols, the primary and secondary amines and formamide. Solvents usable with particular preference are alcohols, and also toluene, xylene, anisole, mesitylene, n-hexane, n-heptane, tris(3,6-dioxaheptyl)amine (TDA), 2-aminomethyltetrahydrofuran, phenetole, 4-methylanisole, 3-methylanisole, methyl benzoate, N-methyl-2-pyrrolidone (NMP), tetralin, ethyl benzoate and diethyl ether. Very particularly preferred solvents are methanol, ethanol, isopropanol, tetrahydrofurfuryl alcohol, 1-methoxy-2-propanol, tert-butanol and toluene, and mixtures thereof.

To achieve particularly good printability or coatability, the composition used in the process according to the invention preferably has a viscosity of 1 mPa·s to 10 Pa·s, especially 1 mPa·s to 100 mPa·s, determined to DIN 53019 parts 1 to 2 and measured at 20° C. Corresponding viscosities can be established by adding polymers, cellulose derivatives, or $SiO_2$ obtainable, for example, under the Aerosil trade name, and especially by means of PMMA, polyvinyl alcohol, urethane thickeners or polyacrylate thickeners.

The substrate which is used in the process according to the invention is preferably a substrate consisting of glass, silicon, silicon dioxide, a metal oxide or transition metal oxide, a metal or a polymeric material, especially PI or PET.

The process according to the invention is particularly advantageously a coating process selected from printing processes (especially flexographic/gravure printing, inkjet printing, offset printing, digital offset printing and screen printing), spraying processes, rotary coating processes ("spin-coating"), dipping processes ("dip-coating"), and processes selected from meniscus coating, slit coating, slot-die coating and curtain coating. The coating process according to the invention is most preferably a printing process.

After the coating and before the conversion, the coated substrate can additionally be dried. Corresponding measures and conditions for this purpose are known to those skilled in the art.

The conversion to an indium oxide-containing layer can be effected by a thermal route and/or by irradiation with electromagnetic, especially actinic, radiation. Preference is given to converting by the thermal route by means of temperatures of greater than 150° C. Particularly good results can be achieved, however, when temperatures of 250° C. to 360° C. are used for conversion.

Typically, conversion times of a few seconds up to several hours are used.

The thermal conversion can additionally be promoted by injecting UV, IR or VIS radiation or treating the coated substrate with air or oxygen before, during or after the thermal treatment.

The quality of the layer obtained by the process according to the invention can additionally be improved further by a combined thermal and gas treatment (with $H_2$ or $O_2$), plasma treatment (Ar, $N_2$, $O_2$ or $H_2$ plasma), laser treatment (with wavelengths in the UV, VIS or IR range) or an ozone treatment, which follows the conversion step.

The present invention further provides the indium oxo alkoxides which have not been described to date in the literature and are of the generic formula $M_xO_y(OR)_z[O(R'O)_eH]_aX_bY_c[R''OH]_d$ where M=In, x=3-25, y=1-10, z=3-50, a=0-25, b=0-20, c=1-20, d=0-25, e=0, 1, R, R', R''=organic radical, X=F, Cl, Br, I, and Y=—$NO_3$, —$NO_2$, where b+c=1-20, and the preferred forms thereof which have already been described above and are likewise not known from the literature, and coating compositions thereof comprising at least one inventive indium oxo alkoxide and at least one solvent.

The composition may comprise either a solvent or a mixture of different solvents. Solvents usable with preference for the process according to the invention in the formulation are aprotic and weakly protic solvents, i.e. those selected from the group of aprotic nonpolar solvents, i.e. of the alkanes, substituted alkanes, alkenes, alkynes, aromatics without or with aliphatic or aromatic substituents, halogenated hydrocarbons, tetramethylsilane, from the group of the aprotic polar solvents, i.e. the ethers, aromatic ethers, substituted ethers, esters or acid anhydrides, ketones, tertiary amines, nitromethane, DMF (dimethylformamide), DMSO (dimethyl sulphoxide) or propylene carbonate, and the weakly protic solvents, i.e. the alcohols, the primary and secondary amines and formamide. Solvents usable with particular preference are alcohols, and also toluene, xylene, anisole, mesitylene, n-hexane, n-heptane, tris(3,6-dioxaheptyl)amine (TDA), 2-aminomethyltetrahydrofuran, phenetole, 4-methylanisole, 3-methylanisole, methyl benzoate, N-methyl-2-pyrrolidone (NMP), tetralin, ethyl benzoate and diethyl ether. Very particularly preferred solvents are methanol, ethanol, isopropanol, tetrahydrofurfuryl alcohol, 1-methoxy-2-propanol, tert-butanol and toluene, and mixtures thereof.

The invention further provides indium oxide-containing layers producible by means of the process according to the invention. Particularly good properties are possessed by the indium oxide-containing layers which are producible via the process according to the invention and are pure indium oxide layers.

The indium oxide-containing layers producible by the process according to the invention are advantageously suitable for the production of electronic components, especially the production of transistors (especially thin-film transistors), diodes, sensors or solar cells.

The example which follows is intended to illustrate the subject-matter of the present invention in detail.

EXAMPLES

Example 1

Synthesis a) Synthesis of the Inventive Material in Methanol

The synthesis is performed with exclusion of atmospheric oxygen.

25 g (1.0% by weight) of indium chloro dimethoxide are dissolved in 3 l of anhydrous methanol. Subsequently, 17.62 g of silver nitrate are added and the mixture is stirred with exclusion of light for 12 h. The solid formed (by-product) is filtered off and the clear solution is concentrated under reduced pressure at 40° C. The remaining solid (product) is dried at 1 mbar for 12 h and transferred.

b) Synthesis of the Inventive Material in 2-Methoxyethanol

The synthesis is performed with exclusion of atmospheric oxygen.

2.5 g (4.9% by weight) of indium chloro dimethoxide are dissolved in 50 ml of anhydrous 2-methoxyethanol. Subsequently, 1.76 g of silver nitrate are added and the mixture is stirred with exclusion of light for 12 h. The solid formed (by-product) is filtered off and the clear solution is concentrated under reduced pressure at 40° C. The remaining solid (product) is dried at 1 mbar for 12 h and transferred.

c) Synthesis of the Inventive Material in Tetrahydrofurfuryl Alcohol

The synthesis is performed with exclusion of atmospheric oxygen.

2.5 g (4.5% by weight) of indium chloro dimethoxide are dissolved in 50 ml of anhydrous tetrahydrofurfuryl alcohol. Subsequently, 1.76 g of silver nitrate are added and the mixture is stirred with exclusion of light for >12 h. The solid formed (by-product) is filtered off and the clear solution is concentrated under reduced pressure at 40° C. The remaining solid (product) is dried at 1 mbar for 12 h and transferred.

Example 2

Processing of TFTs and Stress Tests a) Inventive Example

A doped silicon substrate having an edge length of about 15 mm and having a silicon oxide coating of thickness about 200 nm and finger structures of ITO/Gold was coated with 100 µl of a 5% by weight solution containing the product formed according to example 1 b) in 2-methoxyethanol by spin-coating (2000 rpm for 30 s). After the coating operation, the coated substrate was dried under air at a temperature of 350° C. for 1 h. The semiconductor layer was passivated with a layer of polydimethylsiloxane (PDMSi). The solution of PDMSi from BuOH was applied by means of spin-coating and then the sample was heat treated at 350° C. for 1 h.

a) Comparative Example

A doped silicon substrate having an edge length of about 15 mm and having a silicon oxide coating of thickness about 200 nm and finger structures of ITO/Gold was coated with 100 µl of a 5% by weight solution containing indium chloro dimethoxide in 2-methoxyethanol by spin-coating (2000 rpm for 30 s). After the coating operation, the coated substrate was dried under air at a temperature of 350° C. for 1 h. The semiconductor layer was passivated with a layer of polydimethylsiloxane (PDMSi). The solution of PDMSi from BuOH was applied by means of spin-coating and then the sample was heat treated at 350° C. for 1 h.

BRIEF DESCRIPTION OF THE SEVERAL VIEWS OF THE DRAWINGS

The inventive coating shows (cf.

Figure 1:
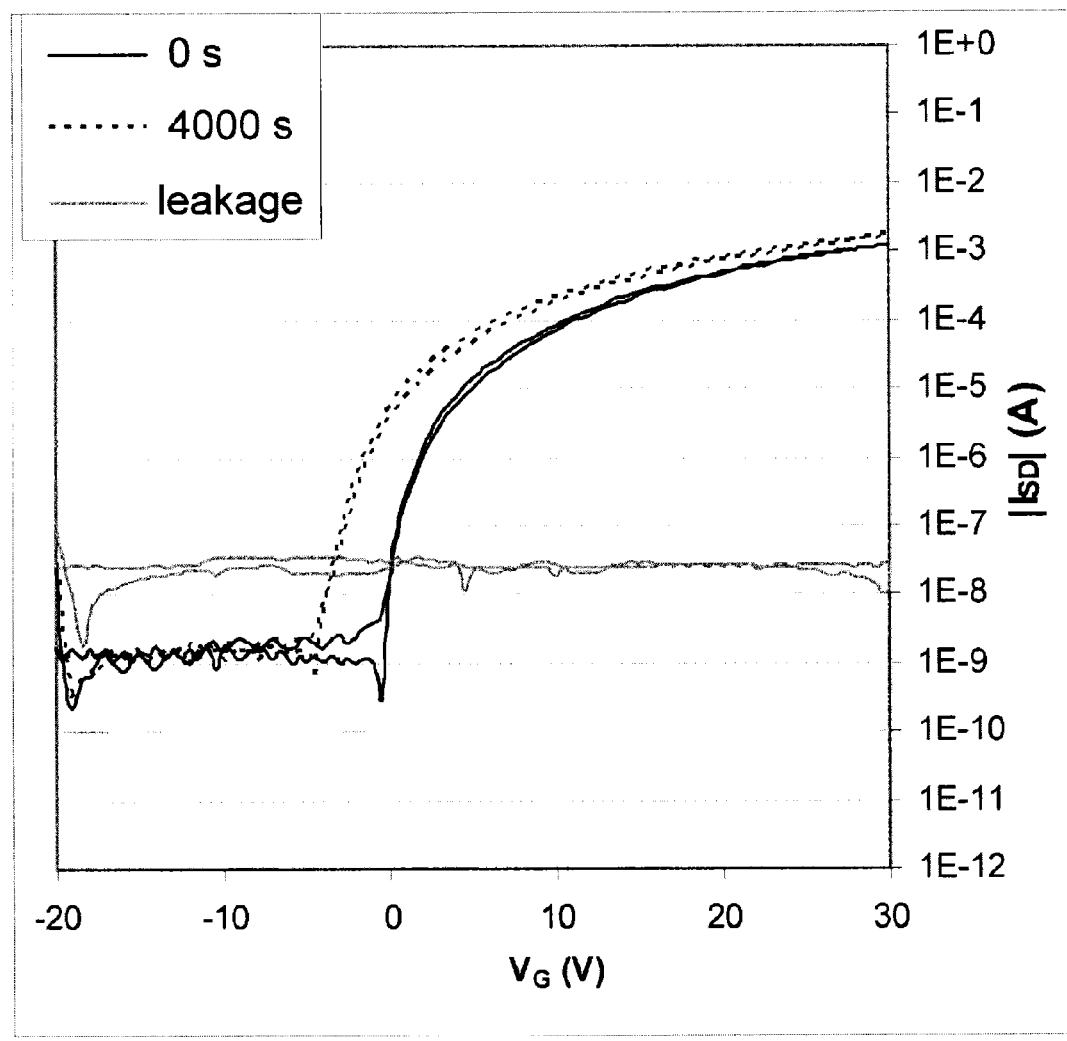
FIG. 1) better electrical stability under negative bias stress (Vgs=−20V, Vds=5V, t=4000 s) than the comparative layer (FIG. 2). The shift in the onset voltage is −3.5V and −7.5V. In addition, the inventive coating has better stability to atmospheric influences in particular.
Figure 2:
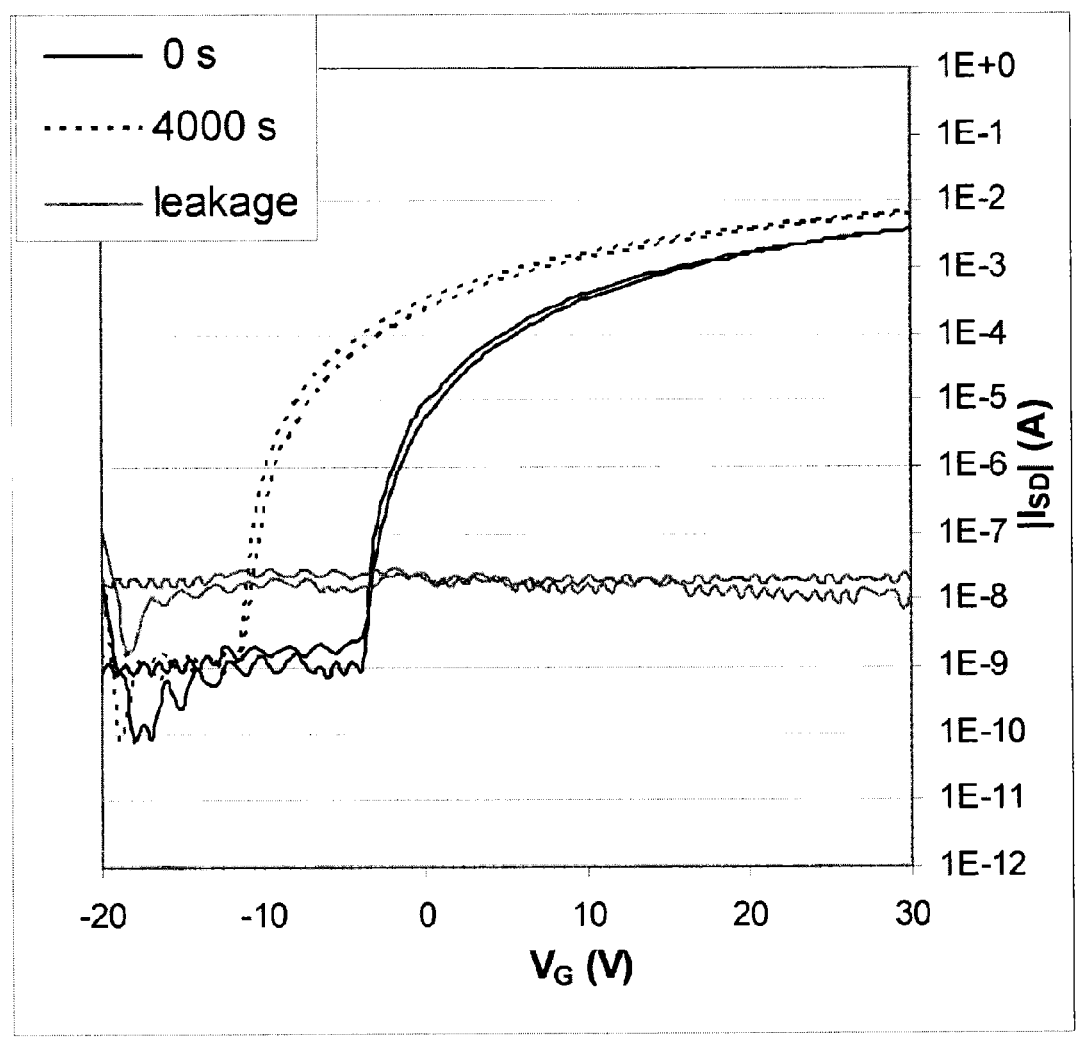

The two figures show the respective transfer characteristics at Vds=10V; TFT (channel width 2000 μm and channel length 20 μm).

The invention claimed is:

1. A liquid phase process for producing an indium oxide-containing layer, comprising:
applying to a substrate, a composition comprising
i) an indium oxo alkoxide of the generic formula

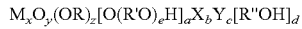

where
x=3-25,
y=1-10,
z=3-50,
a=0-25,
b=0-20,
c=1-20,
d=0-25,
e=0, 1,
M=In,
R, R', R" are each an organic radical,
X=F, Cl, Br, I,
Y=—NO$_3$, —NO$_2$,
with the proviso that b+c=1-20, and
ii) solvent; and
converting the coated substrate to an indium oxide-containing layer.

2. The process according to claim 1, wherein:
the indium oxo alkoxide is of the formula $M_xO_y(OR)_zY_c$,
where x=3-20, y=1-8, z=3-25, c=1-20, OR is a C1-C15-alkoxy, -oxyalkylalkoxy, -aryloxy or -oxyarylalkoxy group and Y is —NO$_3$.

3. The process according to claim 1, wherein
the indium oxo alkoxide is the sole metal oxide precursor in the process.

4. The process according to claim 1, wherein
the indium oxo alkoxide is present in a proportion of 0.1 to 15% by weight, based on the total mass of the composition.

5. The process according to claim 1, wherein
the solvent is an aprotic or weakly protic solvent.

6. The process according to claim 5, wherein
the solvent is selected from the group consisting of methanol, ethanol, isopropanol, tetrahydrofurfuryl alcohol, 1-methoxy-2-propanol, tert-butanol and toluene.

7. The process according to claim 1, wherein
the composition has a viscosity of 1 mPa·s to 10 Pa·s.

8. The process according to claim 1, wherein
the substrate comprises glass, silicon, silicon dioxide, a metal oxide, a transition metal oxide, a metal or a polymeric material.

9. The process according to claim 1, wherein
the composition is an aqueous composition that is applied to the substrate by a process selected from the group consisting of a coating process, a printing process, a spraying process, a rotary coating process, a dipping process, meniscus coating, slit coating, slot-die coating and curtain coating.

10. The process according to claim 1, wherein
the converting is effected thermally at a temperature greater than 150° C.

11. The process according to claim 10, wherein
UV, IR or VIS radiation is injected before, during or after the converting is effected thermally.

12. An indium oxo alkoxide of the generic formula $M_xO_y(OR)_z[O(R'O)_eH]_aX_bY_c[R"OH]_d$
where
x=3-25,
y=1-10,
z=3-50,
a=0-25,
b=0-20,
c=1-20,
d=0-25,
e=0, 1,
M=In,
R, R', R" are each an organic radical,
X=F, Cl, Br, I,
Y=—NO$_3$, —NO$_2$,
with the proviso that b+c=1-20.

13. A coating composition comprising indium oxo alkoxide according to claim 12 and one solvent.

14. An indium oxide-containing layer produced by the process according to claim 1.

15. An electronic component comprising the indium oxide-containing layer according to claim 14.

16. The electronic component according to claim 15, wherein the electronic component is selected from the group consisting of a transistor, a diode, a sensor and a solar cell.

17. The process according to claim 1, further comprising drying the coated substrate before converting the coated substrate to an indium oxide-containing layer.

18. The process according to claim 1, wherein:
the indium oxo alkoxide is of the formula $M_xO_y(OR)_zY_c$,
where x=3-15, y=1-5, z=10-20, c=4-10, R is —CH$_3$, —CH$_2$CH$_3$, —CH$_2$CH$_2$OCH$_3$, —CH(CH$_3$)$_2$, —CH(CH$_3$)CH$_2$OCH$_3$, —C(CH$_3$)$_3$ or

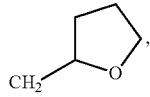

and Y=NO$_3$.

* * * * *